(12) United States Patent
Qin et al.

(10) Patent No.: US 8,431,726 B2
(45) Date of Patent: Apr. 30, 2013

(54) PREPARATION METHOD OF (3S,4S)-3-HEXYL-4-((R)-2-HYDROXYTRIDECYL)-OXETAN-2-ONE AND THE PRODUCT OF THAT METHOD

(75) Inventors: Yong Qin, Sichuan Province (CN); Xianglin Deng, Chongqing (CN); Xuan Zhou, Sichuan Province (CN); Guofeng Yu, Chongqing (CN); Ke Wang, Sichuan Province (CN); Hao Song, Sichuan Province (CN); Xiaolin Wang, Chongqing (CN); Shan Huang, Chongqing (CN)

(73) Assignees: Chongqing Zhien Pharmaceutical Co., Ltd.; Sichuan University

( * ) Notice: Subject to any disclaimer, the term of this patent is extended or adjusted under 35 U.S.C. 154(b) by 139 days.

(21) Appl. No.: 12/990,111

(22) PCT Filed: May 26, 2008

(86) PCT No.: PCT/CN2008/071075
§ 371 (c)(1),
(2), (4) Date: Oct. 28, 2010

(87) PCT Pub. No.: WO2009/143664
PCT Pub. Date: Dec. 3, 2009

(65) Prior Publication Data
US 2011/0046400 A1      Feb. 24, 2011

(51) Int. Cl.
C07D 305/12       (2006.01)
(52) U.S. Cl.
USPC ...................................................... 549/328
(58) Field of Classification Search .................. 549/328
See application file for complete search history.

(56) References Cited

FOREIGN PATENT DOCUMENTS
CN          1765892 A        5/2006

OTHER PUBLICATIONS

Case-Green et al Synlett, 1991, 781-782.*
Ma et al. Org. Lett., 2006, 8, 4497-4500.*
Yang et al, Tetrahedron, vol. 53, No. 48, pp. 16471-16488, 1997.*
Case-Green, Stephen C., et al., "Asymmetric Synthesis of (−)-tetrahydrolipstatin," Synlett 1991, No. 11, pp. 781-782, ISSN: 0936-5214 p. 781, Scheme 3.
Luo, Zhiwei et al., "The Reduction of Carbonyl Group by the System of Sodium Borohydride," Guangdong Chemical Industry 2005, No. 3, pp. 21, 31, 41, ISSN: 1001-1865.0.

(Continued)

*Primary Examiner* — Nizal Chandrakumar
(74) *Attorney, Agent, or Firm* — Blank Rome LLP

(57) ABSTRACT

The present invention relates to a method for the preparation of (3S,4S)-3-hexyl-4-((R)-2-hydroxytridecyl)-oxetan-2-one and a product of the method. The method includes the following steps: a) reducing a substance represented by formula (II) to obtain a substance represented by formula (III), and then oxidizing the substance represented by formula (III) to form a substance represented by formula (IV); b) acylating n-octanoic acid to obtain n-octanoyl chloride using thionyl dichloride, then condensing the obtained n-octanoyl chloride with 2-mercapto-pyridine under basic condition to form a substance represented by formula (V), and then converting the substance represented by formula (V) to a substance represented by formula (VI); c) reacting the substance obtained in the step a) with the substance obtained in the step b) under catalytic condition of Lewis acid to generate a substance represented by formula (VII), and then reacting with a Lewis acid. The meanings of the signs in these formulas are the same as those in the description.

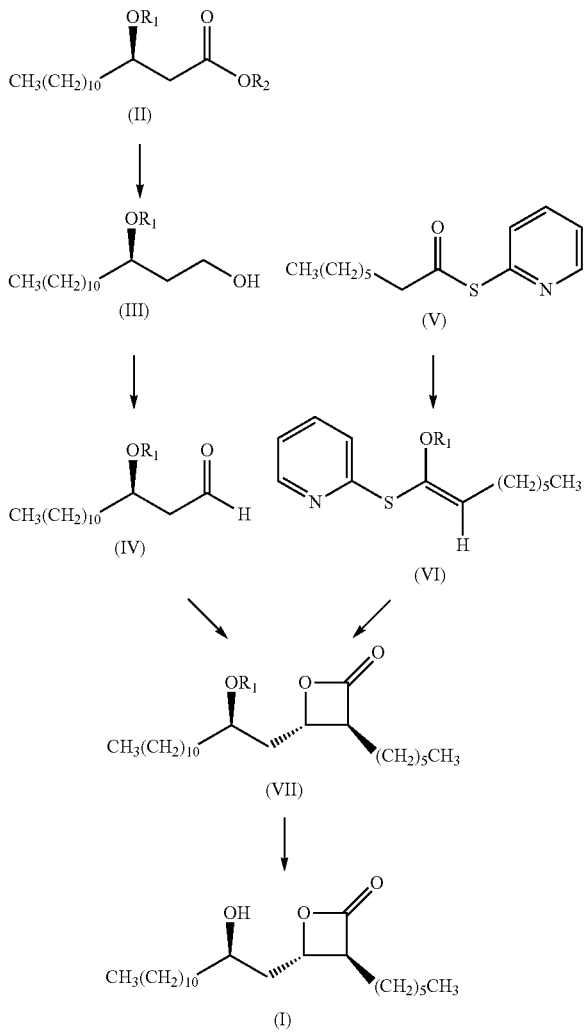

32 Claims, No Drawings

OTHER PUBLICATIONS

Yin, Jian et al., "Total Synthesis of (−)-Tetrahydrolipstatin by the Tandem Mukaiyama-aldol Lactonization," Chinese Chemical Letters, vol. 16, No. 11, pp. 1448-1450, 2005.

Hanessian, Stephen et al., "Total Synthesis of (−)-Tetrahydrolipstatin," J. Org. Chem, 1993, 58, 7768-7781.

* cited by examiner

PREPARATION METHOD OF (3S,4S)-3-HEXYL-4-((R)-2-HYDROXYTRIDECYL)-OXETAN-2-ONE AND THE PRODUCT OF THAT METHOD

CROSS-REFERENCE TO RELATED APPLICATIONS

The present application claims the benefit of International Patent Application No. PCT/CN2008/071075, filed May 26, 2008, the entire disclosures are incorporated by reference herein.

FIELD OF THE INVENTION

The present invention relates to a preparation method of β-lactone intermediates and the products prepared by this method.

BACKGROUND OF THE INVENTION

Along with the improvement of people's living standards, and because of the diet not quite reasonable, the number of people suffering from obesity has been increasing for years. Because it may trigger or aggravate diabetes, fatty liver, and cardiovascular system diseases, etc., obesity has become one of the serious diseases threatening human health. A weight-reducing aid, Orlistat, developed by Roche, Switzerland, is a non-systemic active and specific gastric and pancreatic lipase inhibitor with long and potent activity, which may inactivate the lipases in the gastrointestinal tract by covalently bonding the active serine residues, thus blocking the hydrolysis and absorption of about 30% fat in food, which results in body weight loss. Researches demonstrate, while long-term weight control in obese patients, this drug can reduce incidence of hyperlipemia, hypertension and hyperglycemia as well as other obesity-related diseases. Orlistat has advantages of little systemic absorption, non-accumulation during repeated administration, low serum concentration, and non-tolerance etc, while its side effects are mainly of gastrointestinal reactions. As the first OTC weight-reducing aid approved by U.S. Food and Drug Administration (FDA), Orlistat has been marketed in over 100 countries. Currently about 8 million people worldwide are taking Orlistat, which ranks the number one sales of weight-reducing drugs in the worldwide market. Therefore, there is a promising future for the development of Orlistat. At present, API of Orlistat products used in clinic is mainly prepared by reducing natural lipstatin which is used as raw material, but the natural lipstatin is not readily available so that Orlistat prepared by this method is of high production cost, and the patients are not able to afford it. Thus, the preparation of Orlistat by total synthesis process helps reduce the cost of medication for patients. By analyzing the structure of Orlistat, it can be seen that the β-lactone intermediate is an important intermediate for the synthesis of Orlistat, and the target product Orlistat can be made from this intermediate through Mitsunobu reaction. Therefore, the development of a preparation method of β-lactone intermediate which has short synthetic route and low-cost, suitable for industrial production, would bring important prospect and economic value.

The β-lactone intermediate mentioned in the present invention is (3S,4S)-3-hexyl-4-((R)-2-hydroxytridecyl)-oxetan-2-one, its structure formula represented by formula (I):

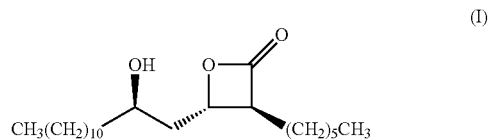

The reaction equation of preparing Orlistat from β-lactone intermediate is as follows:

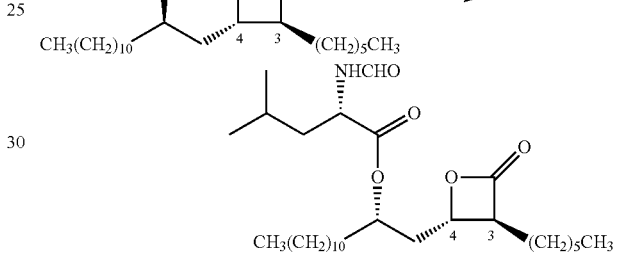

wherein, 3-situs and 4-situs of β-lactone intermediate has been labeled.

The literature search shows that there are mainly three methods for construction of the β-lactone intermediate: (1) constructing the β-lactone intermediate through condensation and cyclization of alkyl-aldehyde with alkenyl ether or silyl ketene having hexyl side chain in the presence of Lewis acid as catalyst; (2) firstly synthesizing a β-hydroxyl acid through Aldol condensation reaction of alkyl aldehyde with n-octanoic acid ester or through tri-substituted six-membered lactone intermediate or its analogue as key intermediate, then synthesizing the β-lactone intermediate through the lactonization of the β-hydroxyl acid; and (3) directly constructing the β-lactone intermediate through photocatalytic alkylation using alkenyl lactone as raw material. Among the above three methods, if compared with the method (2), the method (1) needs less reaction steps and is more favorable for reducing industrial production costs thus having obvious cost advantage; although the method (3) has less steps, it needs expensive reagents and specific reaction environments for photocatalytic alkylation, not favorable for the realization of industrial production. It can be seen that at present the method (1) is a more favorable synthesis route to reduce the production cost. The synthesis routes of the three methods mentioned above are as follows:

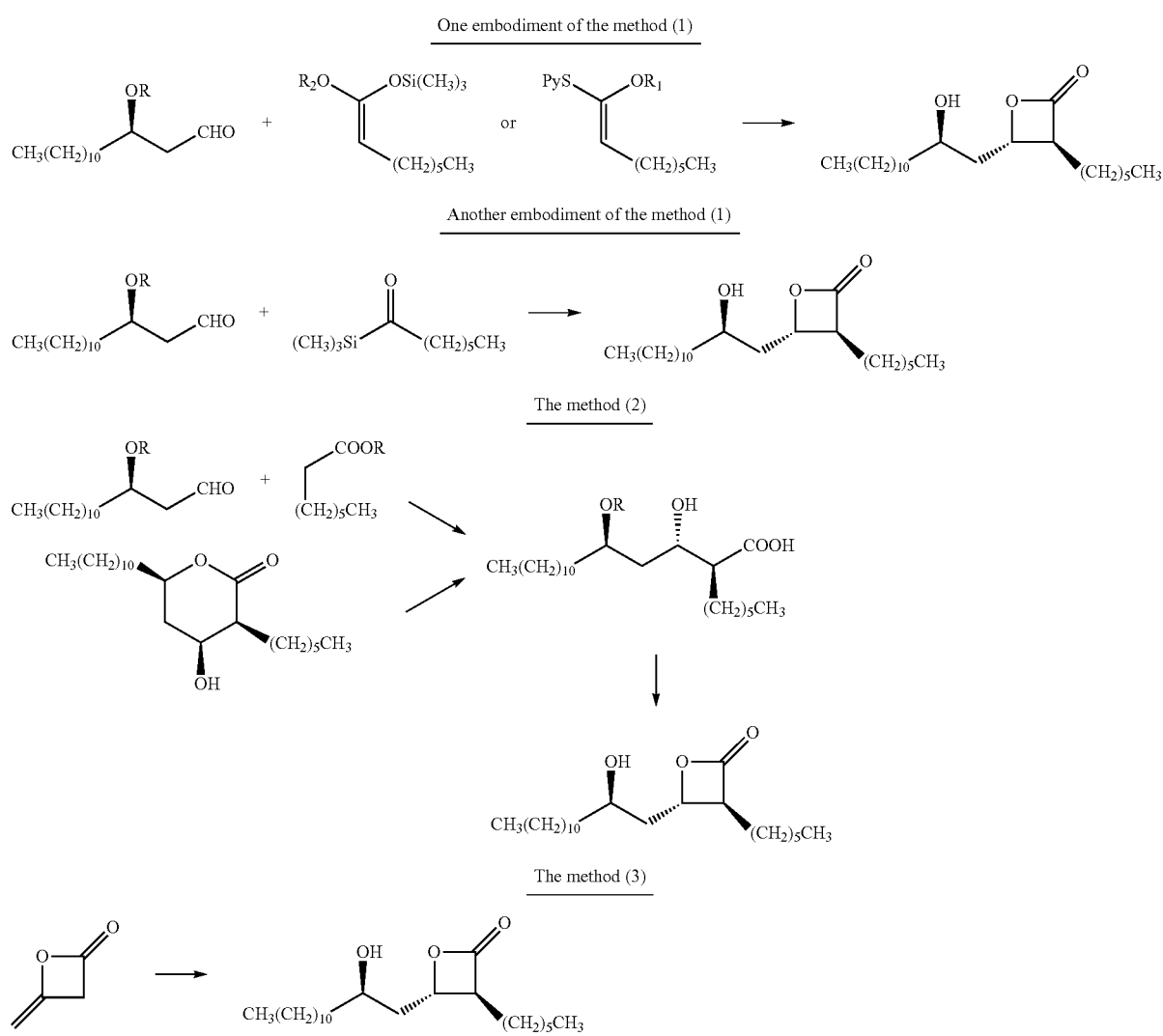

In the above three methods, R represents a hydroxyl protecting group.

As seen from the main synthesis methods of β-lactone intermediate above mentioned, in the method (1), alkyl-aldehyde is a key precursor compound for the total synthesis of Orlistat. Currently the commonest synthesis method of alkyl-aldehyde is a one-step reaction of reducing alkyl acid ester using DIBAL reagent at a low temperature of −78° C. to obtain the aldehyde, and the β-hydroxyl protecting group used therein is usually benzyl, tetrahydropyranyl, tert-butyldimethylsilyl and the like. However, the reductive reagents DIBAL used in this method are relatively expensive and the low reaction temperature required is a harsh condition, so that the method has low economic value and is not suitable for large scale production in industry. The method of construction of β-lactone intermediate using reagent DIBAL is as follows:

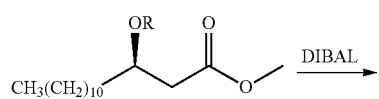

-continued

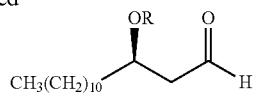

wherein, R represents a hydroxyl protecting group.

SUMMARY OF THE INVENTION

One object of the present invention is to provide a preparation method of a β-lactone intermediate, which is low expectation for reaction condition and is economical and practical, thereby suitable for large scale production in industry.

Another object of the present invention is to provide a product prepared by the above mentioned preparation method of a β-lactone intermediate.

To achieve the above objects, the present invention adopts the following technical solutions:

A method for preparation of a compound represented by formula (I),

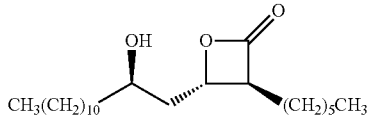
(I)

comprising the following steps:

a) reducing a substance represented by formula (II) to form a substance represented by formula (III) using a reduction reagent,

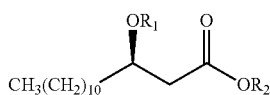
(II)

wherein, in the formula (II), $R_1$ represents a hydroxyl protecting group, and $R_2$ represents a straight or branched, saturated or unsaturated alkyl group,

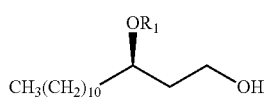
(III)

wherein, $R_1$ in the formula (III) has the same meaning as in the formula (II), then oxidizing the substance represented by formula (III) to form a substance represented by formula (IV) using an oxidation reagent under basic condition,

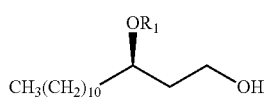
(IV)

wherein, $R_1$ in the formula (IV) has the same meaning as in the formula (II), wherein the reduction reagent is selected from the group consisting of dimethyl sulfide borane, dimethyl sulfide borane/sodium borohydride, sodium borohydride/aluminum trichloride, sodium borohydride/iodine, sodium borohydride/trimethylchlorosilane and sodium borohydride;

b) acylating n-octanoic acid to obtain n-octanoyl chloride by using thionyl dichloride, then condensing the obtained n-octanoyl chloride with 2-mercaptopyridine under basic condition to form a substance represented by formula (V).

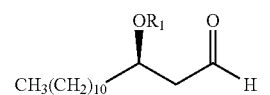
(V)

then reacting the substance represented by formula (V) under basic condition to form a substance represented by formula (VI):

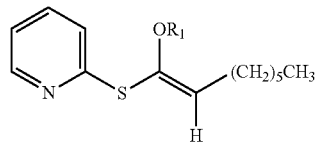
(VI)

wherein $R_1$ in the formula (VI) has the same meaning as in the formula (II);

c) reacting the substance obtained in the step a) with the substance obtained in the step b) under catalytic condition of Lewis acid to form a substance represented by formula (VII),

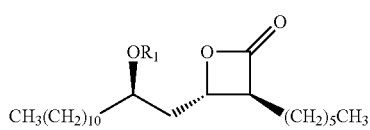
(VII)

wherein, $R_1$ in the formula (VII) has the same meaning as it in the formula (II), then reacting with an acid to form the compound represented by formula (I);

the sequence of step a) and step b) is alterable.

The substances prepared from the step a) and the step b) are independent from each other, i.e., one may conduct the step a) first, or the step b) first, or both the step a) and the step b) simultaneously, or in other combination manners.

The illustration is made for each step respectively below:

Step a)

In the substance represented by formula (II), $R_1$ represents a hydroxyl protecting group. Hydroxyl protection is a means commonly used in chemical synthesis. Many ways can be used to protect hydroxyl groups, referring to 'Protective Groups in Organic Synthesis', (East China University of Science and Technology Press, 1 Ed. 2004, Chapter 2). In the present invention, the principle of choosing a hydroxyl protecting group is the hydroxyl protecting group being easy to be removed. For example, $R_1$ can be selected from tert-butyldimethylsilyl, benzyl and tetrahydrofuryl, preferable tert-butyldimethylsilyl.

$R_2$ represents a straight or branched, saturated or unsaturated alkyl group, and can be selected from alkyl groups having 1-8 carbon atoms, such as methyl, ethyl, propyl, isopropyl, n-butyl, n-pentyl, n-hexyl, n-heptyl and the like, preferably methyl.

The reduction reagents in the step can be selected from the group consisting of dimethyl sulfide borane, dimethyl sulfide borane/sodium borohydride, sodium borohydride/aluminum trichloride, sodium borohydride/iodine, sodium borohydride/trimethylchlorosilane and sodium borohydride; preferably sodium borohydride/aluminum trichloride. The reaction using the reduction reagents described here requires a relatively moderate reaction condition, and can be conducted at room temperature rather than a temperature of −78° C. The reaction equation is:

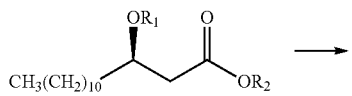

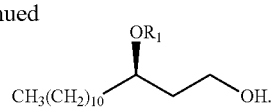

The oxidation reagent in the step can be selected from commonly used oxidants such as active manganese dioxide, Swern oxidation reagent and pyridinium chlorochromate, preferably pyridinium chlorochromate. Swern oxidation reagent is a moderate oxidation reagent consisting of dimethyl sulfoxide and oxalyl chloride. The reaction equation is:

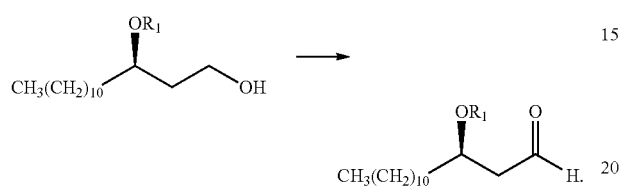

The oxidation reaction is carried out under basic condition, which can use triethylamine, sodium acetate, 1,5-diazabicyclo[4.3.0]non-5-ene and diisopropylethylamine and pyridine, preferably triethylamine. An improvement for this reaction is using silica gel as carrier additive. Research showed that the use of silica gel as carrier additive not only accelerates the reaction, but also allows the post-treatment simple and easy to handle, which is favorable for the realization of industrial production and has significant cost advantage. The solvent used in the oxidation reaction is selected from toluene, tetrahydrofuran, dichloromethane, chloroform, 1,2-dichloroethane, n-hexane, ethyl ether and isopropyl ether, preferably dichloromethane. The temperature of the oxidation reaction is between −78° C. and 100° C., preferably between 20° C. and 30° C., more preferably 25° C.

Step b)

First, the n-octanoic acid is acylated by using thionyl dichloride to obtain n-octanoyl chloride, and the reaction equation is:

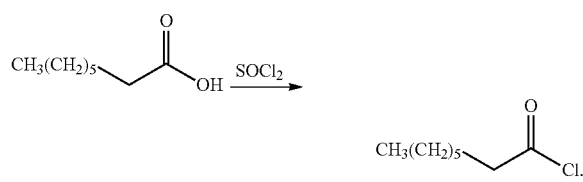

The solvent used in this reaction can be N,N-dimethylformamide.

Then, the n-octanoyl chloride is reacted with 2-mercaptopyridine under basic condition, and the reaction equation is:

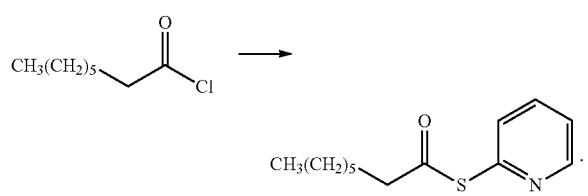

The alkaline used in this reaction can be triethylamine, and the solvent may be dichloromethane.

Then the reaction below is carried out under basic condition:

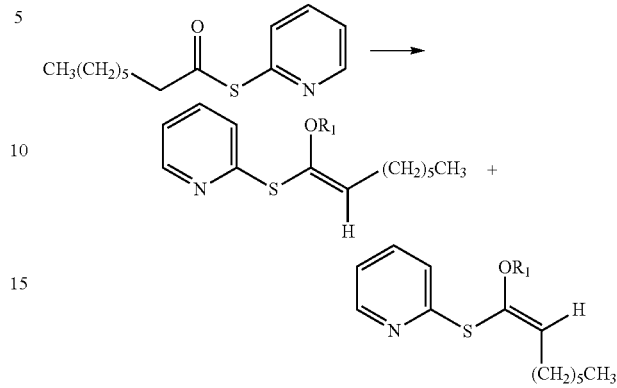

wherein, $R_1$ has the same meaning as in the step a). The reaction produces two cis-trans-isomers. The used alkaline is selected from the group consisting of lithium diisopropylamide/N,N-dimethylformamide/triethylamine, lithium diisopropylamide/hexamethyl phosphoric triamide/triethylamine, lithium diisopropylamide/hexamethyl phosphoric triamide, lithium diisopropylamide/triethylamine, lithium hexamethyldisilazide/hexamethyl phosphoric triamide/triethylamine, lithium hexamethyldisilazide/hexamethyl phosphoric triamide, lithium hexamethyldisilazide/triethylamine, potassium hexamethyldisilazide/hexamethyl phosphoric triamide/triethylamine, sodium hexamethyldisilazide/hexamethyl phosphoric triamide/triethylamine and lithium hexamethyldisilazide/1,3-dimethyl-3,4,5,6-tetrahydro-2-pyrimidinone/triethylamine, preferably lithium diisopropylamide/hexamethyl phosphoric triamide/triethylamine. The used solvent is selected from toluene, benzene, tetrahydrofuran, dioxane, dichloromethane and N,N-dimethylformamide, preferably tetrahydrofuran. The reaction time may be 10 to 120 minutes, preferably 20 to 30 minutes. The reaction temperature is −40° C. to −85° C., preferable −75° C. to 80° C., more preferably −78° C. The yield of the reaction can be 91% or more. The E/Z ratio of the resulting two cis-trans-isomers can be up to 98:1, wherein E represents trans-isomer and Z represents cis-isomer. The studies known showed that trans-isomer is more preferred than the cis-isomer to produce β-lactone intermediate.

Step c)

The substance obtained in the step a) and the substance obtained in the step b) react under the catalytic condition of Lewis acid, and the reaction equation is:

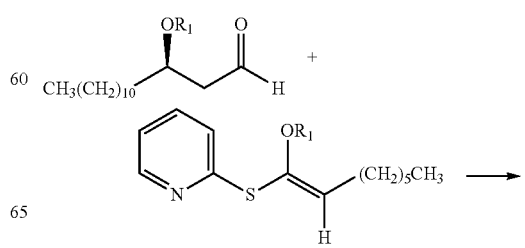

-continued

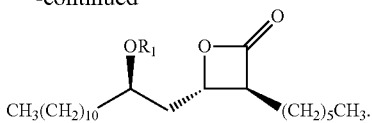

first reagent second reagent product

A dual catalyst consisting of zinc chloride and copper bromide can be used in this reaction, the solvent can be dichloromethane, and the reaction temperature can be −20° C. to 30° C. The use of copper bromide, on one hand, can allow reacting with the second reagent to form a copper ionic intermediate, thereby catalyzing the formation of ring structure of β-lactone intermediate; on the other hand, it can consume the excess of the second reagent so as to greatly simplify purification process. The subsequent step can be carried out without any column chromatography after the reaction. Undesired isomers of the product as represented in the reaction equation are also produced in this reaction, and the quantity of the undesired isomers is less than one eighth of the product as represented in the reaction.

Then reaction with acid removes the protecting group R1, and the reaction equation is:

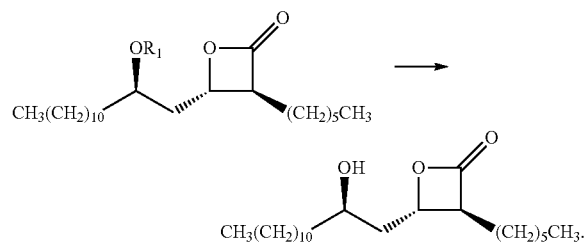

The acid used in this reaction may be hydrofluoric acid, preferably hydrofluoric acid with a concentration of 35 to 45%, more preferably hydrofluoric acid with a concentration of 40%. The used solvent may be acetonitrile.

After the completion of reaction, recrystallization can be carried out to separate and prepare an optically pure β-lactone intermediate. Solvent used for recrystallization is selected from n-hexane, n-pentane, petroleum ether, ethyl ether and ethanol, and the mixture of petroleum ether and ethyl ether is preferred. The purity of β-lactone intermediate isolated from recrystallization is more than 99.7%, and the purity of the diastereomer is more than 99.9%.

The present invention also provides a β-lactone intermediate prepared by the aforementioned method.

Compared with the prior art, the method for preparation of β-lactone intermediate described in the present invention does not need string conditions and is economical and practical. Purification and separation of intermediates are not necessary in the whole reaction process, and after the three step of reaction, the yield of the target product β-lactone intermediate can achieve more than 30%, therefore favorable for mass industrial production. In the preparation methods of the present invention, the reduction process of the step a) is not carried under a harsh condition of the temperature of −78° C., and has a relatively short reaction time as well as a low price of the reduction reagents; and the oxidation reagent used in the oxidation process is also not expensive. The step b) uses n-octanoic acid as raw material, needs no column chromatography treatment until producing the generation of the compound of formula (VI), which greatly increases the effectiveness of the preparation and favor for the realization of industrial production.

SPECIFIC MODES FOR CARRYING OUT THE INVENTION

The technical solution of the present invention is further illustrated by way of examples.

Example 1

Step a)

For the preparation of (R)-3-tert-butyl dimethylsilaneoxy tetradecanol, reaction equation is:

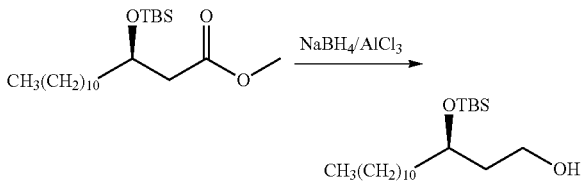

wherein TBS represents tert-butyl dimethyl silyl. 380.1 g (0.95 mol) of (R)-3-tert-butyl dimethylsilaneoxy tetradecanoic acid methyl ester was dissolved into 1.5 L of dichloromethane and was stirred at room temperature, followed by adding 58.8 g (1.55 mol) of sodium borohydride. 77.5 g (0.58 mol) of aluminum trichloride was slowly added under ice bath condition, and then continuing the reaction under the ice bath condition. After 0.5 h, the temperature was controlled between 5 and 20° C., and about 1.0 L of hydrochloride acid (0.5 mol/L) was dropped to neutral. The reaction solution was extracted in turn by petroleum ether (2×1.0 L, meaning using 1.0 L to extract twice) and water (2×1.0 L), and the combined aqueous layer was extracted by petroleum ether (3×0.7 L). The organic layers were combined and dried through anhydrous sodium sulfate and filtered. Vacuum evaporation of solvent gave 347.9 g of product of pale yellow oil. The yield is 98.5%. $^1$H NMR (400 MHz, CDCl$_3$) δ 3.88-3.94 (m, 1H), 3.81-3.87 (m, 1H), 3.66-3.75 (m, 1H), 2.49 (t, J=5.2 Hz, 1H), 1.79-1.85 (m, 1H), 1.60-1.68 (m, 1H), 1.51-1.53 (m, 2H), 1.25-1.30 (m, 18H), 0.90 (s, 9H), 0.88 (t, J=6.8 Hz, 3H), 0.09 (s, 3H), 0.08 (s, 3H) ppm.

Next is the preparation of (R)-3-tert-butyl dimethylsilaneoxy tetradecyl aldehyde. The reaction equation is:

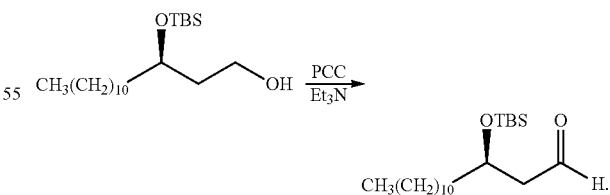

375.0 g (1.74 mol) of pyridinium chlorochromate was dissolved into 0.9 L of dichloromethane and 346.9 g of silica gel of 300-400 mesh was added. After stirred for 10 minutes at room temperature, 13.9 mL (0.10 mol) of triethylamine was added. Then the solution of 346.9 g (1.00 mol) of (R)-3-tert-butyl dimethylsilaneoxy tetradecanol in dichloromethane was added dropwisely to the reaction solution within 10 minutes, and then stirred to react for 5 hours. 0.9 L of petroleum ether was added to the reaction solution and stirred for another 15 minutes, filtered and washed by petroleum ether (4×0.7 L). Vacuum evaporation of the filtrate gave 340.0 g of brown oil, which is (R)-3-tert-butyl dimethylsilaneoxy tetradecyl aldehyde, yielding 77.8%. ¹H NMR (400 MHz, CDCl₃) δ 9.81 (s, 1H), 4.10-4.20 (m, 1H), 2.51 (dd, J=5.6, 2.4 Hz, 2H), 1.47-1.55 (m, 2H), 1.26-1.30 (m, 18H), 0.88 (s, 9H), 0.88 (t, J=3.6 Hz, 3H), 0.07 (s, 3H), 0.06 (s, 3H) ppm.

Step b)

For the preparation of n-octanoyl chloride, the reaction equation is:

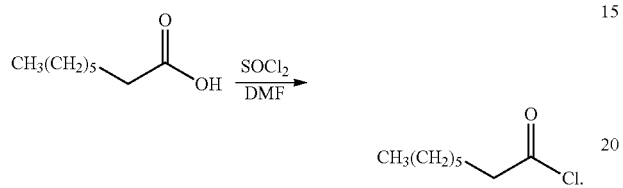

912.0 g (6.34 mol) of n-octanoic acid and 640 mL (8.89 mol) of thionyl dichloride were mixed at room temperature, lots of gas was generated and the reaction solution was stirred until the gas no more increasing. Then 5 mL of N,N-dimethylformamide was added, and after stirred for 2 hours at room temperature, the solution was heated to reflux. After reflux for 4 hours, to remove the excess thionyl dichloride under vacuum by evaporation, and to collect the fraction of vacuum distillation at 68 to 70° C./0.096 mPa, obtaining 914.0 g pale yellow oil of n-octanoyl chloride, with a yield of 88.8%.

Then the preparation of the substance represents by formula (V), the reaction equation is:

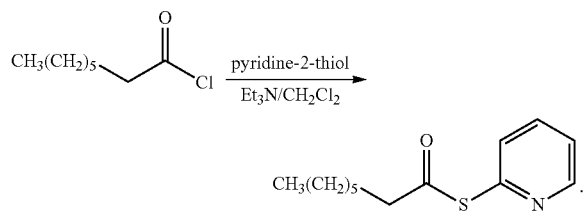

500.0 g (4.50 mol) of 2-mercaptopyridine and 700.0 mL (5.03 mol) of triethylamine were dissolved into 4.0 L of dichloromethane. 753.5 mL (4.41 mol) of n-octanoyl chloride was slowly added under ice bath condition and then the reaction continued at room temperature. After 0.5 hour, 3.0 L water was added to quench the reaction, the organic layer was separated and extracted by 10% Na₂CO₃ (3×2.0 L) and saturated brine (2×2.0 L) respectively. The organic layers are combined and dried through anhydrous sodium sulfate and filtered. Vacuum evaporation of the solvent resulted brown-red oil, and the oil was dissolved in 5.6 L ethyl acetate and was washed by 10% K₂CO₃ (2×2.0 L), water (2×2.0 L) and saturated brine (2×2.0 L). The organic layer was stirred with 250.0 g anhydrous sodium sulfate and 50.0 g activated carbon to dry and decolorize for overnight. To filter and collect the filtrate, and by vacuum evaporation it gave 1053.0 g of brown-red oil, the substance represented by formula (V), yielding 100%.

Then, for the preparation of the substance represented by formula (VI), the reaction equation is:

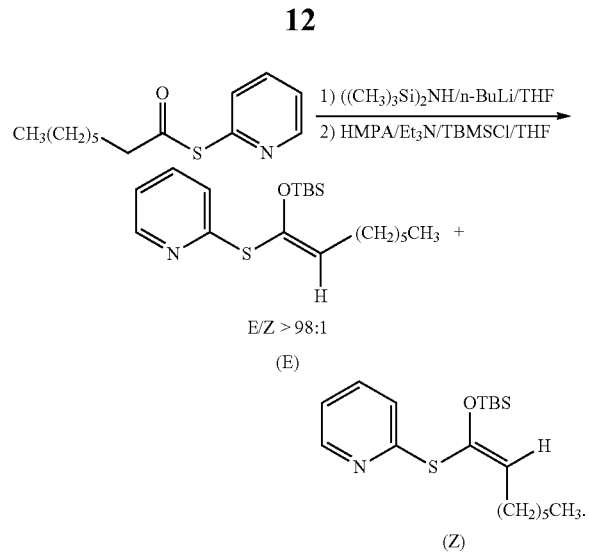

230.3 mL (1.10 mol) of (Me₃Si)₂NH was dissolved into 400 mL of tetrahydrofuran and cooled to −10° C. with stirring. 405.1 mL (1.01 mol) of n-butyl lithium was slowly dropped into the solution within about 30 minutes, and then 50 mL tetrahydrofuran was added. After 1 hour reaction at 0° C., the reaction solution was cooled to −78° C., and 353.5 mL (2.53 mol) of triethylamine, 440.0 mL (2.53 mol) of hexamethyl phosphoric triamide and 100 mL t-butyl dimethyl chlorosilane (165.3 g, 1.1 mol) in tetrahydrofuran, were quickly added in turn, each for about 15 minutes. 200.0 g (0.84 mol) of the substance of formula (V) was dissolved into 100 mL of tetrahydrofuran, cooled to −78° C., and dropped into the above solution in 30 to 40 minutes. The reaction was continued for 20 to 30 minutes at −78° C. After adding 1.5 L of petroleum ether, the solution rose to room temperature, 500 mL water was added to quench the reaction and separate the organic layer. The aqueous layer was extracted by petroleum ether (3×500 mL), and the organic layers were combined and dried through anhydrous sodium sulfate. Filtration and vacuum evaporation resulted 270.5 g of brown oil, the product in the equation right side, with a yield of 91.2%, and E/Z>98:1. For the product, ¹H NMR (400 MHz, CDCl₃) δ 7.14-7.43 (m, 4H), 5.28 (t, J=7.2 Hz, 1H), 2.14-2.26 (m, 2H), 1.29-1.41 (m, 8H), 0.88 (s, 9H), 0.80-0.94 (m, 3H), 0.09 (s, 3H), 0.04 (s, 3H) ppm.

Step c)

For the preparation of the substance represented by formula (VII), the reaction equation is:

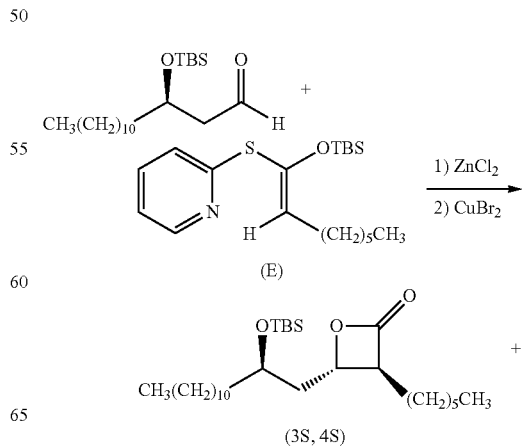

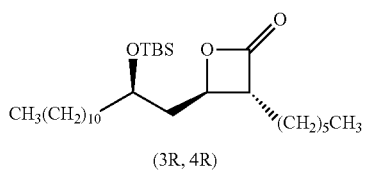

(3R, 4R)

12.0 g (35.06 mmol) of the substance obtained from the step a), 13.5 g (38.5 mmol) of the substance obtained from the step b) and 14.5 g (106.4 mmol) of anhydrous zinc chloride were dissolved in 160 mL of dichloromethane and stirred at room temperature. After 61 hours of reaction, 60 mL of sodium dihydrogen phosphate/disodium hydrogen phosphate buffer (pH=7) was added and stirred for 30 minutes. Silica gel was used to aid in filtering and the filtered cake was washed by 150 mL of dichloromethane. The filtrate was extracted by water (2×250 mL) and the combined organic layers was dried through anhydrous sodium sulfate and concentrated to a brown-yellow oil, the oil was dissolved in 100 mL of dichloromethane and 10.2 g (45.9 mmol) of copper bromide was added. After stirred for 2 hours, the reaction solution was concentrated to dark green viscous liquid. This viscous liquid was dissolved in 50 mL of petroleum ether and was filtered with aid of silica gel of 200 to 300 mesh. The filtered cake was washed by mixture solvents of petroleum ether/ethyl acetate=50/1, and the filtrate was extracted in turn by 10% potassium carbonate (2×100 mL), water (2×100 mL) and saturated brine (2×100 mL). The organic layers were combined and dried through anhydrous sodium sulfate and vacuum evaporation gave a transparent yellow oil liquid, i.e. the crude product with in which the ratio of diastereoisomers was 8:1.

The reaction equation for preparing optically pure β-lectone intermediate is:

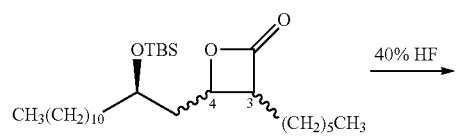

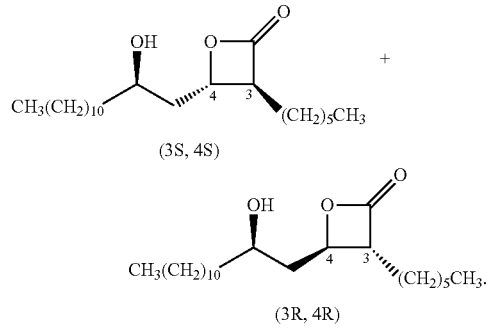

(3S, 4S)

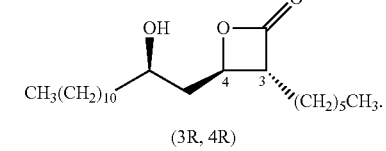

(3R, 4R)

The crude product obtained from the last step was dissolved into 100 mL of acetonitrile and 25 mL of 40% hydrofluoric acid solution was added. The reaction was stayed at room temperature overnight. 500 mL of petroleum ether was added and the reaction solution was extracted in turn by water (3×100 mL) and saturated sodium bicarbonate (2×100 mL). The organic layer was washed by saturated brine to neutral and then the combined organic layers were dried through anhydrous sodium sulfate. Filtration and vacuum evaporation gave a yellow-brown oil and this oil was recrystallized using 40 mL of petroleum ether to result a yellow solid. The obtained yellow solid was recrystallized by petroleum ether, petroleum ether/ethyl ether mixture or n-hexane, n-pentane and n-pentane/ethyl ether mixture solvent to obtain 4.4 g of white needle crystal β-letone intermediate (3S,4S), yielding 35.7%. $[\alpha]^{20}_D=-41°$ (c 0.4, CHCl$_3$); reverse phase HPLC analysis of said crystal showed a chemical purity of greater than 99.7%, (chromatographic conditions: C$_{18}$ column; mobile phase water:methanol=90:10; flow rate 1.0 mL/min; 210 nm; t$_R$=11.7 min); more than two types of chiral HPLC gave a diastereoisomers purity of greater than 99.9% (chromatographic conditions: AS-H column; mobile phase isopropanol:hexane=2:98; flow rate 1.0 mL/min; 210 nm; t$_1$=8.1 min; t$_2$=9.8 min; or AD-H column; mobile phase isopropanol:hexane=5:95; flow rate 1.0 mL/min; 210 nm; t$_1$=6.9 min; t$_2$=6.3 min; wherein t$_1$ is retention time of (3S,4S)-β-lectone intermediate, and t$_2$ is retention time of (3R,4R)-β-lectone intermediate). $^1$H NMR (400 MHz, CDCl$_3$) δ 4.48-4.53 (m, 1H), 3.80-3.82 (m, 1H), 3.24-3.28 (m, 1H), 1.73-1.95 (m, 4H), 1.26-1.50 (m, 28H), 0.86-0.90 (m, 6H) ppm.

During the performing of the step a), the invention sifted reduction reagents and oxidation reagents, which are showed in Table 1 and Table 2.

TABLE 1

Choice of reduction reagents

| Reduction reagents | Solvent | Reaction conditions | Yield or reaction results |
|---|---|---|---|
| lithium aluminium hydride | tetrahydrofuran | room temperature | less target product (less than 10%), mainly diol after removing TBS |
| | ethyl ether | room temperature | |
| | toluene | room temperature | |
| | n-hexane | room temperature | |
| | ethylene glycol dimethyl ether | room temperature | |
| | isopropyl ether | room temperature | |
| dimethyl sulfide borane | tetrahydrofuran | N$_2$ protection/room temperature | 59% |
| | n-hexane | N$_2$ protection/room temperature | 93% |
| dimethyl sulfide borane/sodium borohydride | tetrahydrofuran | N$_2$ protection/room temperature | 63% |
| sodium borohydride/aluminum trichloride | ethylene glycol dimethyl ether | room temperature | 98.46% |
| sodium borohydride/iodine | tetrahydrofuran | room temperature | less than 5% |

TABLE 1-continued

Choice of reduction reagents

| Reduction reagents | Solvent | Reaction conditions | Yield or reaction results |
|---|---|---|---|
| sodium borohydride/trimethylchlorosilane | tetrahydrofuran | room temperature-reflux | less than 5% |
| sodium borohydride | PEG-400 | room temperature-reflux | less than 5% |
| sodium borohydride | tert-butanol: methanol = 5:1 | room temperature-reflux | less than 5% |

TABLE 2

Choice of oxidation reagents

| Oxidation reagents | Solvent | Reaction Conditions | Yield or reaction results |
|---|---|---|---|
| active manganese dioxide | toluene | room temperature-reflux | Less target product (less than 10%), most of feedstock remained |
| | dichloromethane | room temperature-reflux | Less target product (less than 10%), most of feedstock remained |
| | n-hexane | room temperature-reflux | 45% |
| Dess-Martin oxidation reagents | dichloromethane | room temperature | 80% |
| Swern oxidation reagent | dichloromethane | −78° C. | 57% |
| | | −60° C. | 45% |
| | | −45° C. | 20% |
| | | −20° C. | Almost no target product |
| pyridinium chlorochromate (PCC) | n-hexane | room temperature | Less target product (less than 10%), most of feedstock remained |
| | toluene | room temperature | Less target product (less than 10%), most of feedstock remained |
| | dichloromethane | room temperature | 70% |
| | dichloromethane | silica gel/triethylamine | 77.80% |
| | dichloromethane | silica gel/pyridine | 74% |
| | dichloromethane | silica gel/sodium acetate | 72% |

During the performing of the step b), the invention sifted reaction conditions, which is showed in Table 3.

TABLE 3

Choice of reaction conditions

| Alkaline system | Protection group | Solvent | Reaction Conditions | Yield or reaction results |
|---|---|---|---|---|
| lithium diisopropylamide/hexamethyl phosphoric triamide/triethylamine | trimethyl silyl | toluene dioxane benzene dichloromethane N,N-dimethyl-formamide tetrahydrofuran | reaction time: 30 min, temperature: −78° C. | Most of intermediated unreacted, less target product (less than 15%) |
| | t-butyl dimethyl silyl | toluene dioxane benzene dichloromethane N,N-dimethyl-formamide | reaction time: 30 min, temperature: −78° C. | 72.0% less target product (less than 15%), mainly n-octanoic acid after removing activated group 2-mercapto-pyridine |
| | | tetrahydrofuran | | 91.2% |
| | | tetrahydrofuran | reaction time: 25 min, temperature: −78° C. | 91.8% |

TABLE 3-continued

| Alkaline system | Protection group | Solvent | Reaction Conditions | Yield or reaction results |
|---|---|---|---|---|
| | | tetrahydrofuran | reaction time: 30 min, temperature: −60° C. | 45.2% |
| | | tetrahydrofuran | reaction time: 30 min, temperature: −40° C. | 25.7% |
| | | tetrahydrofuran | reaction time: 1 h, temperature: −78° C. | 80.6% |
| | | tetrahydrofuran | reaction time: 2 h, temperature: −78° C. | 67.7% |
| lithium hexamethyldisilazide/triethylamine | t-butyl dimethyl silyl | Tetrahydrofuran | reaction time: 30 min, temperature: −78° C. | 35.0% |
| potassium hexamethyldisilazide/hexamethyl phosphoric triamide/triethylamine | t-butyl dimethyl silyl | Tetrahydrofuran | | less than 15% |
| sodium hexamethyldisilazide/hexamethyl phosphoric triamide/triethylamine | t-butyl dimethyl silyl | Tetrahydrofuran | | less than 15% |
| lithium hexamethyldisilazide/1,3-dimethyl-3,4,5,6-tetrahydro-2-pyrimidinone/triethylamine | t-butyl dimethyl silyl | Tetrahydrofuran | | 75.3% |
| lithium diisopropylamide/N,N-dimethylformamide/triethylamine | t-butyl dimethyl silyl | Tetrahydrofuran | | less than 15% |
| lithium diisopropylamide/hexamethyl phosphoric triamide/triethylamine | t-butyl dimethyl silyl | Tetrahydrofuran | | less than 15% |
| lithium diisopropylamide/hexamethyl phosphoric triamide | t-butyl dimethyl silyl | Tetrahydrouran | | less than 15% |
| lithium diisopropylamide/triethylamine | t-butyl dimethyl silyl | Tetrahydrofuran | | less than 15% |

Above mentioned are the preferred embodiments of the present invention. It should be understood to those skilled in the art that numerous variations and modifications could be made without departing from the principle of the invention, which are deemed to be within the scope of the present invention.

What is claimed is:

1. A preparation method for a compound represented by formula (I),

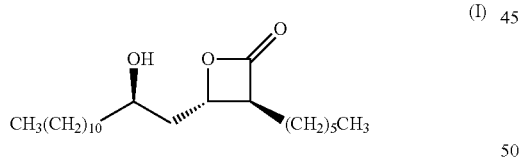

comprising the following steps:
a) reducing a substance represented by formula (II) to obtain a substance represented by formula (III) using sodium borohydride/aluminum trichloride as a reduction reagent,

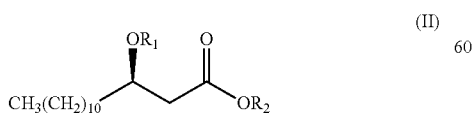

wherein, in the formula (II), $R_1$ represents a hydroxyl protecting group, and $R_2$ represents a straight or branched alkyl group,

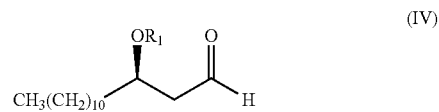

wherein $R_1$ in the formula (III) has the same meaning as in the formula (II), then, oxidizing the substance represented by formula (III) to form a substance represented by formula (IV) using an oxidation reagent under basic condition,

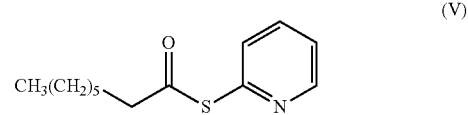

wherein $R_1$ in the formula (IV) has the same meaning as in the formula (II);

b) acylating n-octanoic acid to obtain n-octanoyl chloride using thionyl dichloride, and then condensing the obtained n-octanoyl chloride with 2-mercaptopyridine under basic condition to form a substance represented by formula (V), (V)

then, the substance represented by formula (V) is converted to a substance represented by formula (VI) under basic condition:

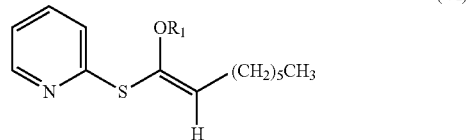

(VI)

wherein R₁ in the formula (VI) has the same meaning as in the formula (II);

c) reacting the substance obtained in the step a) with the substance obtained in the step b) under catalytic condition of Lewis acid to form a substance represented by formula (VII),

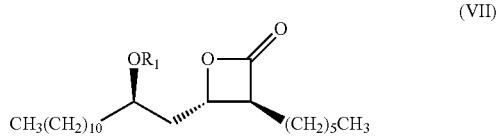

(VII)

wherein, R₁ in the formula (VII) has the same meaning as in the formula (II), then, reacting with an acid to obtain the compound represented by formula (I);

wherein, the sequence of the step a) and the step b) is alterable.

2. The preparation method of claim 1, which, after the step c), further comprises:

d) recrystallizing to separate the compound represented by formula (I).

3. The preparation method of claim 1, wherein R₁ is selected from tert-butyldimethylsilyl, benzyl and tetrahydrofuryl.

4. The preparation method of claim 1, wherein R₂ is an alkyl group having 1-8 carbon atoms.

5. The preparation method of claim 1, wherein the oxidation reagent in the step a) is selected from active manganese dioxide, Swern oxidation reagent and pyridinium chlorochromate.

6. The preparation method of claim 1, wherein the basic condition in step a) is provided by an alkaline compound selected from triethylamine, sodium acetate, 1,5-diazabicyclo[4.3.0]non-5-ene and diisopropyl-ethylamine and pyridine.

7. The preparation method of claim 1, wherein, when the substance represented by formula (III) is oxidized by the oxidation reagent to form the substance represented by formula (IV) in the step a), a silica gel is used as carrier additive.

8. The preparation method of claim 7, wherein, when the substance represented by formula (III) is oxidized by the oxidation reagent to form the substance represented by formula (IV) in the step a), a solvent selected from toluene, tetrahydrofuran, dichloromethane, chloroform, 1,2-dichloroethane, n-hexane, ethyl ether and isopropyl ether is used.

9. The preparation method of claim 8, wherein, when the substance represented by formula (III) is oxidized by the oxidation reagent to form the substance represented by formula (IV) in the step a), a temperature of −78° C. to 100° C. is used.

10. The preparation method of claim 1, wherein, when n-octanoic acid is acylated by thionyl dichloride to form n-octanoyl chloride in the step b), N,N-dimethylformamide is used as solvent.

11. The preparation method of claim 1, wherein, when the n-octanoyl chloride condensed with 2-mercaptopyridine under basic condition to obtain the substance represented by formula (V) in the step b), triethlyamine is used as alkaline and dichloromethane is used as solvent.

12. The preparation method of claim 1, wherein, when the substance represented by formula (V) is converted to the substance represented by formula (VI) under basic condition in the step b), an alkaline composition selected from the groups consisting of lithium diisopropylamide/N,N-dimethylformamide/triethylamine, lithium diisopropylamide/hexamethyl phosphoric triamide/triethylamine, lithium diisopropylamide/hexamethyl phosphoric triamide, lithium diisopropylamide/triethylamine, lithium hexamethyldisilazide/hexamethyl phosphoric triamide/triethylamine, lithium hexamethyldisilazide/hexamethyl phosphoric triamide, lithium hexamethyldisilazide/triethylamine, potassium hexamethyldisilazide/hexamethyl phosphoric triamide/triethylamine, sodium hexamethyldisilazide/hexamethyl phosphoric triamide/triethylamine and lithium hexamethyldisilazide/1,3-dimethyl-3,4,5,6-tetrahydro-2-pyrimidinone/triethylamine is used.

13. The preparation method of claim 12, wherein, when the substance represented by formula (V) is converted to the substance represented by formula (VI) under basic condition in step b), a solvent selected from toluene, benzene, tetrahydrofuran, dioxane, dichloromethane and N,N-dimethylformamide is used.

14. The preparation method of claim 13, wherein, when the substance represented by formula (V) is converted to the substance represented by formula (VI) under basic condition in step b), a reaction time of 10 min to 120 minutes is used.

15. The preparation method of claim 14, wherein, when the substance represented by formula (V) is converted to the substance represented by formula (VI) under basic condition in step b), a reaction temperature of −40° C. to −85° C. is used.

16. The preparation method of claim 1, wherein, a dual catalyst is used in the reaction for producing the substance represented by formula (VII) in the step c), wherein the dual catalyst is zinc chloride and copper bromide.

17. The preparation method of claim 16, wherein, during the reaction for producing the substance represented by formula (VII) in the step c), dichloromethane is used as solvent and a reaction temperature of −20° C. to 30° C. is used.

18. The preparation method of claim 17, wherein, during the reaction with the acid to form the compound represented by formula (I) in the step c), the acid used is hydrofluoric acid.

19. The preparation method of claim 18, wherein, during the reaction with the acid to form the compound represented by formula (I) in the step c), acetonitrile is used as solvent.

20. The preparation method of claim 2, wherein a solvent selected from n-hexane, n-pentane, petroleum ether, ethyl ether and ethanol is used for the recrystallization.

21. The preparation method of claim 3, wherein R₁ is tert-butyldimethylsilyl.

22. The preparation method of claim 4, wherein R₂ is methyl.

23. The preparation method of claim 5, wherein the oxidation reagent in the step a) is pyridinium chlorochromate.

24. The preparation method of claim 6, wherein the alkaline compound is triethylamine.

25. The preparation method of claim 8, wherein the solvent is dichloromethane.

26. The preparation method of claim 9, wherein, when the substance represented by formula (III) is oxidized by the oxidation reagent to form the substance represented by formula (IV) in the step a), a temperature of 20° C. to 30° C. is used.

27. The preparation method of claim 12, wherein the alkaline composition is lithium diisopropylamide/hexamethyl phosphoric triamide/triethylamin.

28. The preparation method of claim 13, wherein the solvent is tetrahydrofuran.

29. The preparation method of claim 14, wherein the reaction time is 20 minutes to 30 minutes.

30. The preparation method of claim 16, wherein the reaction temperature is −75° C. to −80° C.

31. The preparation method of claim 18, wherein hydrofluoric acid is used at 35 to 45%.

32. The preparation method of claim 20, wherein the solvent is a mixture of petroleum and ethyl ether.

* * * * *